United States Patent [19]

Diggens et al.

[11] 4,263,104
[45] Apr. 21, 1981

[54] ELECTROCHEMICAL MONITORING

[75] Inventors: Albert A. Diggens, Weston; James W. Ross, Jr., Cambridge, both of Mass.

[73] Assignee: Orion Research Incorporated, Cambridge, Mass.

[21] Appl. No.: 93,258

[22] Filed: Nov. 13, 1979

[51] Int. Cl.$^3$ ............................................. G01N 27/46
[52] U.S. Cl. ............................. 204/1 T; 204/195 M; 204/195 G
[58] Field of Search ........... 204/1 T, 1 F, 1 B, 195 R, 204/195 M, 195 G

[56] References Cited

U.S. PATENT DOCUMENTS

| | | | |
|---|---|---|---|
| 3,431,182 | 3/1969 | Frant | 204/1 B |
| 3,563,874 | 2/1971 | Ross et al. | 204/1 B |
| 3,672,962 | 6/1972 | Frant et al. | 204/1 F |
| 3,846,257 | 11/1974 | Riseman et al. | 204/1 F |
| 3,894,917 | 7/1975 | Riseman et al. | 204/1 B |
| 3,915,831 | 10/1975 | Riseman et al. | 204/1 F |
| 3,964,988 | 6/1976 | Riseman et al. | 204/1 F |
| 4,131,428 | 12/1978 | Diggens | 204/1 T |
| 4,154,659 | 5/1979 | Zetter | 204/1 F |
| 4,154,660 | 5/1979 | Micko | 204/1 F |
| 4,157,283 | 6/1979 | Zetter | 204/1 F |

Primary Examiner—T. Tung
Attorney, Agent, or Firm—John B. Miller

[57] ABSTRACT

An improved flow independent method for electrochemical monitoring of a sample stream for the total concentration of a series of ionic species of the form $X^{-n}$, $H_mX^{-n+m}$ where n varies from 1 to m and $X^{-n}$ is an anion selected from the group consisting of fluoride ion, $F^-$, and sulfide ion $S^{-2}$. The pH of the sample stream is adjusted to a value below the $pk_a$ of the neutral most protonated species of the series. A first electrode sensitive to the activity of $X^{-n}$ is placed in the adjusted stream. The electric potential developed thereby is measured. A second electrode sensitive to the activity of hydrogen ion $H^+$ is also placed in the adjusted stream. The electric potential developed thereby is also measured. The potential difference between the first and second electrode is a measure of the total concentration of the series $X^{-n}$, $H_mX^{-n+m}$.

5 Claims, 3 Drawing Figures

TESTS IN .01m na₂S pH ADJUSTED W/
HCl AND NaOH

ELECTROCHEMICAL MONITORING

BACKGROUND OF THE INVENTION

1. Field of Invention

This invention relates to electrochemical analytical systems and more particularly to continuous, flow independent, monitoring of sample streams for the total concentration of a series of ionic species.

2. Prior Art Statement

The present invention relates to the flow independent monitoring of the total concentration of a series of ionic species of the form $X^{-n}$, $H_mX^{-n+m}$ where m varies from 1 to n and $X^{-n}$ is an anion selected from the group consisting of fluoride ion $F^-$, and sulfide ion $S^{-2}$. For example, the measurement of total sulfide concentration, that is $H_2S$, $HS^-$, and $S^{-2}$ has long been an important factor in the treatment of industrial process streams. Sewage treatment plants, pulp and paper manufacturers, and textile producers test for total sulfide content in effluent streams to protect pipes from corrosion, and to limit noxious odors. Further attention was given to these species by the federal standards for industrial air which were promulgated on May 29, 1971 in Federal Register Vol. 36, No. 105, regulating the allowable amounts of hydrogen sulfide, and hydrogen fluoride in workroom air. Continuous monitoring of total fluoride is important in the plating and transistor manufacturing industries where the make-up of rinse baths are continually checked. Municipal and bottled water plants also need to make continuous measurements of total fluoride, that is, HF and $F^-$, in their streams.

Electrodes specific to fluoride ion $F^-$, and sulfide ion $S^{-2}$, have been known in the literature and in the marketplace. U.S. Pat. No. 3,431,182 issued Mar. 4, 1969 to Frant et al. disclosed a fluoride ion sensitive electrode. U.S. Pat. No. 3,672,962 issued June 27, 1972 to Frant et al. disclosed a sulfide ion sensitive electrode. Neither of the above electrodes measure the total concentration of the anion together with the concentration of its protonated species.

An alternate approach to measuring $H_2S$ was disclosed by Riseman et al. in U.S. Pat. No. 3,915,831, issued Oct. 28, 1975. A fluoride electrode is used as a reference electrode in conjunction with a sulfide ion sensitive electrode. The reference electrode can also be a pH glass type electrode or a sodium sensitive glass type electrode, but if these latter two are used, pH must be carefully controlled. The present invention contemplates the use of a pH electrode not as a reference, but as a $H^+$ ion sensitive device, in contradistinction to the Riseman disclosure. The use of a buffer system is eliminated.

Two patents issued to Riseman et al. describing a method, and an apparatus, respectively, for electrochemical monitoring employ the use of a tag ion and a tag ion electrode as an alarm system. U.S. Pat. No. 3,846,257 issued Nov. 5, 1974 and U.S. Pat. No. 3,964,988 issued June 22, 1976. A reagent stream containing a selected amount of tag ion and ionic species of interest is added to the sample stream. The mixed stream is monitored by two electrodes sensitive to the tag ion and the ion of interest, and a potential difference between the two electrodes is measured. If the sample stream begins to add an amount of the ionic species of interest to the mixed stream, the ratio of concentrations of tag ion to ionic species of interest is altered, the potential difference is altered, and the alarm is triggered. The present invention does not rely on the addition of a reagent stream containing a fixed ratio of tag ion and species of interest to the sample stream.

Various methods have been proposed for adjusting the pH of a sample stream. Diggens disclosed a method in U.S. Pat. No. 4,131,428, issued Dec. 26, 1978, that does not introduce interferring, reactive, or test ions into the sample stream. This method is preferably used in the present invention to adjust the pH of the sample stream to required levels.

SUMMARY OF THE INVENTION

One object of the present invention is to provide a method to potentiometrically measure the total concentration in a sample stream of a series of ionic species of the form $X^{-n}$, $H_mX^{-n+m}$ where m varies from 1 to n and $X^{-n}$ is an anion selected from the group consisting of fluoride ion $F^-$, and sulfide ions $S^{-2}$. A second object is to make the measurement in real time, accurately and in a single step. Another object of the invention is to provide a method for making the measurement without the necessity for precise pH measurement, and further, in a manner that is self-correcting for variations in pH of the sample stream. A further object of the invention is to make such a measurement without a reference electrode, eliminating the liquid junction potential associated therewith.

The objects of the invention are effected by adjusting the pH of the sample stream to a value below the $pk_a$ of the neutral most protonated species of the series. First and second electrodes are placed in the pH adjusted stream, the first electrode being sensitive to the activity of $X^{-n}$ and the second electrode being sensitive to the activity of hydrogen ion $H^+$. The potential difference between the two electrodes is a direct measure of the concentration of the species $H_nX$, which at the adjusted pH is essentially the total concentration of the series in the sample stream. In the pH range below the $pk_a$ of $H_nX$, the two electrodes are self-compensating for changes in $H_nX$ concentration due to changes in pH.

BRIEF DESCRIPTION OF THE DRAWINGS

For a more full understanding of the nature and objects of the present invention, reference should be made to the following detailed description taken in connection with the accompanying drawings wherein.

DETAILED DESCRIPTION OF THE INVENTION

Figure 1:
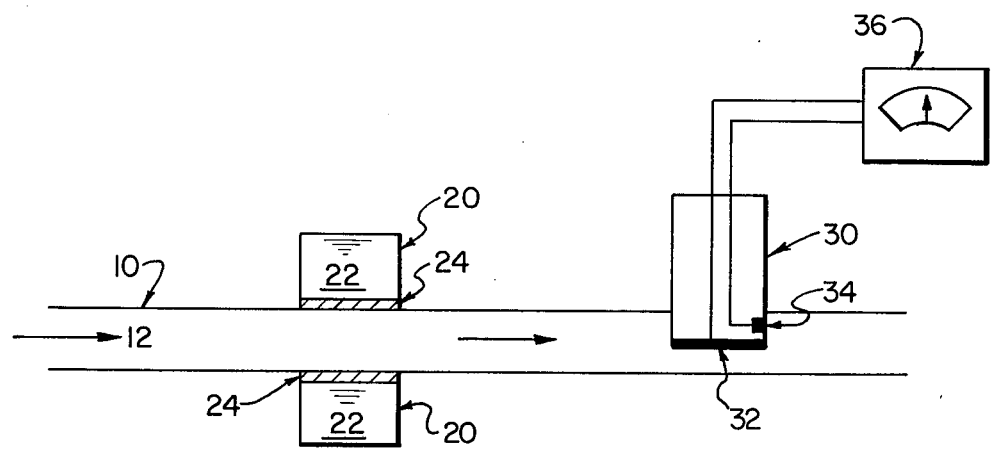
FIG. 1 is a side-elevational schematic view illustrating a system for measuring total concentration according to the principles of the present invention.

Referring now to the drawings, there is shown in FIG. 1 a conduit 10 for conveying a sample stream 12 which is to be monitored for the total concentration of a series of ionic species of the form $X^{-n}$, $H_mX^{-n+m}$, where m varies from 1 to n and $X^{-n}$ is an anion selected from the group consisting of fluoride ion $F^-$, and sulfide ion $S^{-2}$. For the sulfide series, $S^{-2}$, $HS^-$, and $H_2S$, the pH of the sample stream is adjusted to a value below the $pk_a$ for $H_2S$. The pH adjustment must be made without altering the total sulfide content of the sample stream. A preferred method is described by Diggens in U.S. Pat. No. 4,131,428 issued Dec. 26, 1978, incorporated by reference. In this method, acid reagent 22 is placed inside chamber 20, separated from sample stream 12 only by inert, ion-impermeable, non-wetting membrane 24 that is permeable to acid reagent 22. The membrane 24 can be composed of any of the materials described in Diggens, supra, such as silicone polycarbonate copolymer (available as MEM 213 from the General Electric Company, Schenectady, N.Y.). The acid reagent 22 can conveniently be acetic acid, also as described in Diggens. The pH of the sample stream is adjusted to the desired range upon diffusion of acetic acid into the stream, below the $pk_a$ for $H_2S$.

Immersed in the pH adjusted stream is, for the sulfide series, total sulfide electrode system 30, combining two Nernstian electrodes 32 and 34. Electrode 32 is a standard pH electrode sensitive to activity of hydrogen ion $H^+$. Electrode 34 is a sulfide ion electrode. For the fluoride series, electrode 34 would be a fluoride ion electrode. The pH electrode, sulfide ion electrode, and fluoride ion electrode are all available from Orion Research Incorporated of Cambridge, Mass. as ORION$^R$ Models 91-01-00, 94-16, and 94-09, respectively. Electrodes 32 and 34 are electrometrically connected through standard meter 36 to measure the difference in potential therebetween.

Figure 2B:
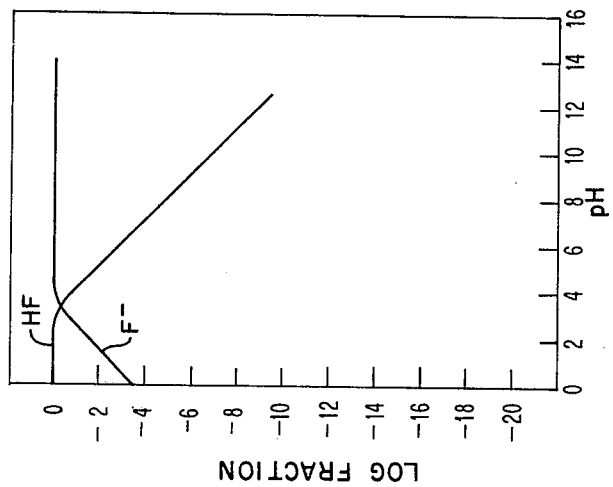
FIGS. 2(a) and 2(b) show plots for each series of the log fraction of total concentration present as each species from pH 0 to pH 14.
Figure 2A:
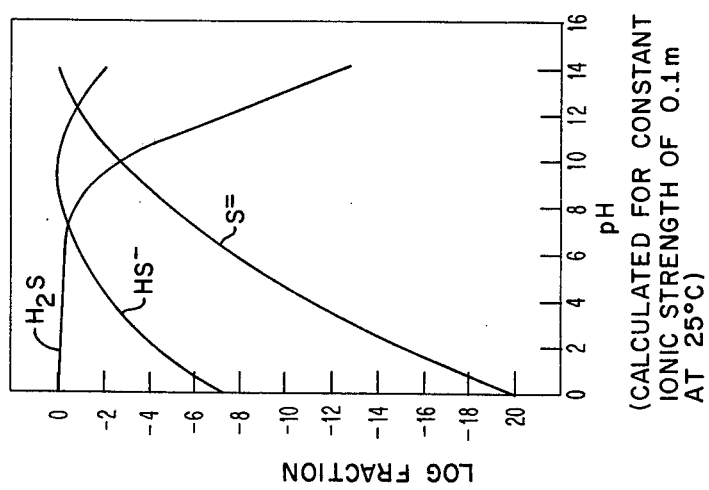

Referring now to FIG. 2, the log fraction of total concentration present as each species from pH 0 to pH 14 for the sulfide and fluoride series is shown. FIG. 2(a) shows that at a pH below the $pk_a$ for $H_2S$, that is pH 7, total sulfide is present predominantly as $H_2S$. Only a small fraction of total sulfide, $10^{-6}$, is present as sulfide ion. At a pH of 4 virtually all total sulfide is present as $H_2S$. FIG. 2b shows that at a pH below the $pk_a$ for HF, that is pH 3.2, total fluoride is present predominantly as HF. Only a small fraction of total fluoride is present as fluoride ion. At a pH of 3 virtually all total fluoride is present as HF.

At these low pH values, metal complexes of these anions will have negligible concentrations and total concentration of each series will have $X^{-n}$, $H_mX^{-n+m}$, where n varies from 1 to m, as the principal $X^-$ containing species.

More particularly, examples I and II below describe the response of meter 36 to total sulfide and fluoride concentrations respectively in sample stream 12.

EXAMPLE I

Sulfide species present with changing pH are described by equations (1), (2) and (3).

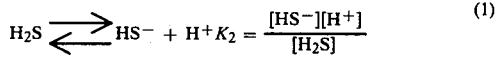  (1)

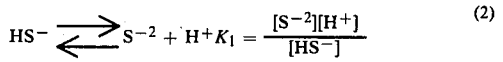  (2)

Combining equations (1) and (2):

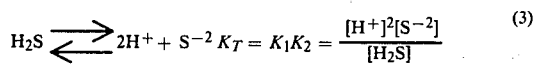  (3)

The response of sulfide electrode 34 is given by equation 4.

$$E_S = E_s^\circ - (RT/2F)\ln[S^{-2}] \quad (4)$$

The response of pH electrode 32 is given by equation 5.

$$E_H = E_H^\circ + (RT/2F)\ln[H^+]^2 \quad (5)$$

substituting the $K_T$ expression from equation 3 into equation 4 for $[S^{-2}]$:

$$E_S = E_s^\circ - (RT/2F)\ln\frac{[H_2S]K_T}{[H^+]^2} \quad (6)$$

$$= E_s^\circ - \frac{RT}{2F}\ln[H_2S] - \frac{RT}{2F}\ln K_T + \frac{RT}{2F}\ln[H^+]^2 \quad (7)$$

Subtracting equation (5) from equation (7), the potential difference measured by meter 36 for total sulfide is obtained.

$$E_S - E_H = E_{TS} = E_{TS}^\circ - \frac{RT}{2F}\ln[H_2S] \quad (8)$$

In a suitably acidified sample, that is roughly 2 pH units below the $pk_a$ for $H_2S$, equation (8) also describes the Nernstian response of these electrodes to total sulfide, since at this low pH, the concentration of $H_2S$ is essentially equal to that of all the sulfides present.

Figure 3:
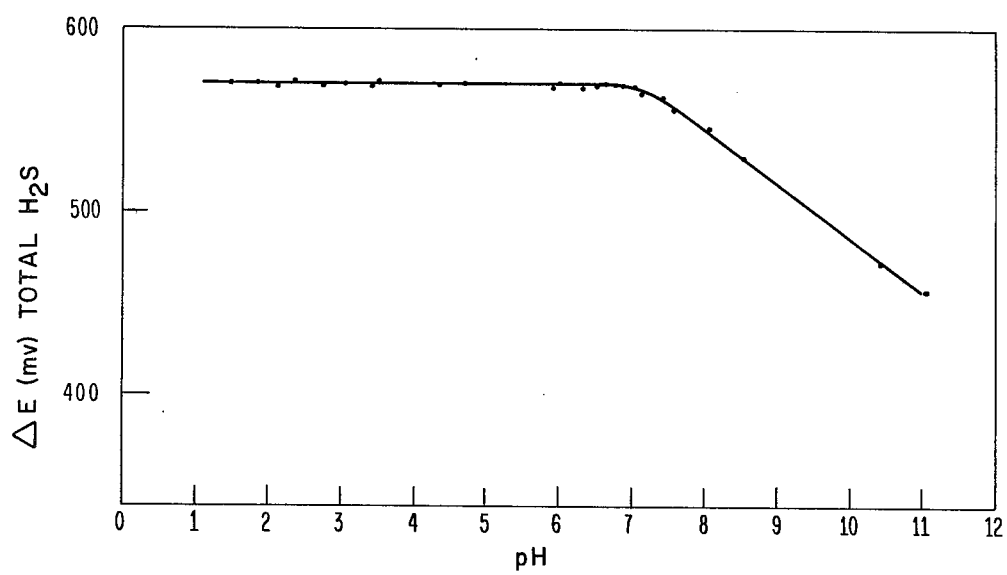
FIG. 3 is a semi-logarithmic graph showing the millivolt response of the $H_2S$ system to small changes in pH.

FIG. 3 presents test results showing that the total sulfide concentration can be accurately and repeatedly measured despite changes in sample stream pH. This is what would be expected by a comparison of equations (5) and (7) indicating that small changes in pH of the system produces no change in the potential difference between the electrodes. As shown in FIG. 3, total sulfide concentration is unaltered with a change in pH so long as the pH is below the $pk_a$ of $H_2S$. In the pH range below the $pk_a$ of $H_2S$, the two electrodes are self compensating for changes in total $H_2S$ concentration due to changes in pH. Increases in $H^+$ ion concentration are compensated with decreases in $S^{-2}$ ion concentration, producing a potential difference measured in millivolts that is constant with small changes in pH.

EXAMPLE II

Fluoride species present with changing pH are described by equation (9).

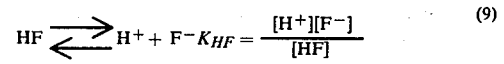  (9)

The response of the fluoride electrode 34 is given by equation (10).

$$E_F = E_F^\circ - (RT/F)\ln[F^-] \quad (10)$$

The response of pH electrode 32 is given by equation (11).

$$E_H = E_H^\circ + \left(\frac{RT}{F}\right)\ln[H^+] \quad (11)$$

Substituting the $K_{HF}$ expression from equation (9) into equation (10) for $[F^-]$:

$$E_F = E_F^\circ - \frac{RT}{F}\ln\frac{K_{HF}[HF]}{[H^+]} \quad (12)$$

$$= E_F^\circ - \frac{RT}{F}\ln K_{HF} - \frac{RT}{F}\ln[HF] + \frac{RT}{F}\ln[H^+] \quad (13)$$

Subtracting equation (11) from equation (13), the potential difference measured by meter 36 for total fluoride is obtained.

$$E_F - E_H = E_{TF} = E°_{TF} - \frac{RT}{F} \ln [HF] \qquad (14)$$

In a suitably acidified sample, that is roughly 2 pH units below the $pk_a$ for HF, equation (14) also describes the Nernstian response of these electrodes to total fluoride. At a pH below the $pk_a$ for HF, that is below pH 3.2, total fluoride is present predominantly at HF. Total fluoride concentration is unaltered with a change in pH so long as the pH is below the $pk_a$ of HF. Increases in $H^+$ ion concentration are compensated with decreases in $F^-$ ion concentration producing a potential difference measured in millivolts that is constant with small changes in pH.

Other systems where the total concentration of weak acids is desired to be measured are analogous. Given an electrode sensitive to small concentrations of anions and appropriate acidification to roughly 2 units below the $pk_a$ of the protonated species, total concentration can be determined using a pH electrode and the anion sensitive electrode in a way that is self-compensating for small changes in pH.

Since various changes may be made in the above method without departing from the scope of the present invention, it is intended that all matter contained in the above description or shown in the accompanying drawings shall be interpreted in an illustrative and not in a limiting sense.

What is claimed is:

1. An improved pH independent method for monitoring of a sample stream for the total concentration of a series of ionic species of the form $X^{-n}$, $H_mX^{-n+m}$, where m varies from 1 to n and $X^{-n}$ is an anion selected from the group consisting of fluoride ion $F^-$, and sulfide ion $S^{-2}$, said method comprising the steps of:
   adjusting or maintaining the pH of the sample stream to a value below the $pk_a$ of the neutral most protonated species of the series;
   placing only a first electrode and a second electrode in the adjusted stream such that the electrodes are in direct contact with the adjusted stream, said first electrode being sensitive to the activity of $X^{-n}$ and said second electrode being sensitive to the activity of hydrogen ion $H^+$; and
   measuring the potential difference developed between the first and second electrode, said difference indicating the total concentration of the series in the stream.

2. Method of claim 1 where the series contains the species $S^{-2}$ ion, $HS^-$ and $H_2S$.

3. Method of claim 2 where the pH is adjusted to a value below 5.

4. Method of claim 1 where the series contains the species $F^-$ ion and HF.

5. Method of claim 4 where the pH is adjusted to a value below 2.5.

* * * * *